`US005506116A`

United States Patent [19]

Daniel et al.

[11] Patent Number: 5,506,116
[45] Date of Patent: Apr. 9, 1996

[54] METHOD AND ELEMENT FOR ASSAY OF CATECHOL AND CATECHOL GENERATING SUBSTANCES

[75] Inventors: Daniel S. Daniel, Rochester; James R. Schaeffer, Penfield, both of N.Y.

[73] Assignee: Johnson & Johnson Clinical Diagnostics, Inc., Rochester, N.Y.

[21] Appl. No.: 8,037

[22] Filed: Jan. 21, 1993

Related U.S. Application Data

[62] Division of Ser. No. 548,395, Jul. 5, 1990, Pat. No. 5,320,946.

[51] Int. Cl.$^6$ .............. C12Q 1/26; C12Q 1/42; C12Q 1/00; G01N 33/48
[52] U.S. Cl. .............. 435/25; 435/21; 435/18; 435/4; 436/63; 436/74
[58] Field of Search .............. 435/25, 18, 26, 435/28, 4, 11, 14, 10, 21; 436/63, 74

[56] References Cited

U.S. PATENT DOCUMENTS

| | | | |
|---|---|---|---|
| 4,089,747 | 5/1978 | Bruschi | 435/10 |
| 4,416,983 | 11/1983 | Roder et al. | 435/25 |
| 4,777,132 | 10/1988 | Green et al. | 435/25 |
| 5,185,249 | 2/1993 | Arter et al. | 435/25 |

OTHER PUBLICATIONS

Webster's Third New International Dictionary, p. 1107 & p. 1299, (1986).
Clin. Chem., 30:1549, 1984 You et al.

Primary Examiner—Douglas W. Robinson
Assistant Examiner—Louise N. Leary

[57] ABSTRACT

A method and multilayer analytical element for the determination of catechol and catechol generating substances such as salicylate is described. A series of enzymatic conversions involving tyrosinase is used to convert catechol to o-quinone and the latter to convert a leuco dye to a colored dye.

10 Claims, No Drawings

METHOD AND ELEMENT FOR ASSAY OF CATECHOL AND CATECHOL GENERATING SUBSTANCES

This is a Divisional of application Ser. No. 548,395, filed 05 Jul. 1990, now U.S. Pat. No. 5,320,946.

FIELD OF THE INVENTION

This invention relates to clinical analyses and, in particular, to a method and element for the assaying catechol, catechol generating substances such as salicylate and enzymes that catalyze generation of catechol.

BACKGROUND OF THE INVENTION

The determination of the catechol generating substance salicylate in biological fluids such as human serum, has diagnostic significance. Acetylsalicylic acid (aspirin) is used as an analgesic and as an anti-inflammatory drug for arthritis. It rapidly hydrolyzes to salicylate which has the therapeutic effect. The therapeutic level as an analgesic is up to 20 mg/dl. For arthritis the level is up to 30 mg/dl. Problems such as headaches, tinnitus, flushing and hyperventilation occur at higher salicylate levels followed by imbalances in the acid-base level. Salicylate levels above 60 mg/dl can be lethal.

One method for assaying salicylate employs the enzymatic conversion of salicylate to catechol catalyzed by salicylate hydroxylase with the accompanying conversion of NADH to $NAD^+$. There is a quantitative correlation between disappearance of NADH, as reflected in a change in optical density at 340 nm, and the concentration of salicylate (You and Bittikofer, Clin. Chem., 30:1549, 1984). The problem is that this method is unsuitable for incorporation into a dry format to be stored over time because of the instability of NADH at low pH and the low extinction coefficient of NADH.

Other problems of existing methods for the determination of salicylate suffer from poor sensitivity of the NADH method, interferences from phenolic and ketoacids normally present in serum, Ferric chloride, time-consuming procedures, inability to measure protein bound salicylate (measure only free salicylate refers to ion selective electrodes), or unsuitability for dry format.

SUMMARY OF THE INVENTION

The present invention provides a colorimetric method for a quantitative assay of catechol, including catechol generating substances such as salicylate, and enzymes that catalyze generation of catechol. The method comprises the steps of:

a) providing a sample suspected of containing catechol, a catechol generating substance such as salicylate or an enzyme that catalyzes generation of catechol; and b) admixing with the sample NADH, tyrosinase, a colorless leuco dye; or alternatively
  i) admixing with the admixture of b) an enzyme, such as salicylate hydroxylase, selected to catalyze the conversion of the catechol generating substance to catechol; or
  ii) admixing with the admixture of b) an enzyme substrate that generates catechol.

c) determining colorimetrically the quantitative presence in the sample of catechol, the catechol generating substance such as salicylate, or the enzyme that catalyzes generation of catechol from the enzyme substrate.

The present invention also provides an analytical element for assaying catechol, including any catechol generating substances such as salicylate, or an enzyme that catalyzes generation of catechol from the catechol generating substance (enzyme substrate). The element comprises one layer containing tyrosinase and another layer comprising NADH and a colorless form of a leuco dye in either layer.

The NADH free layer contains the enzyme selected to catalyze generation of catechol by reaction with NADH when the assay is directed to such catechol generating substances. Alternatively the element contains a substrate for a particular enzyme when the objective of the assay is that particular enzyme. The inclusion in the element of salicylate hydroxylase for the assay of its substrate, salicylate is a preferred embodiment of this aspect of the invention.

The present invention further provides a dry multilayer analytical element for quantitatively assaying salicylate comprising a support bearing at least 2 layers, wherein:

a) one layer comprises NADH, and b) the other layer comprises tyrosinase and a colorless leuco dye.

This element also includes salicylate hydroxylase when the assay is conducted by omitting a step of adding the salicylate hydroxylase to the sample to be assayed.

The method and element of this invention obviates the problems associated with measuring the disappearance of NADH since the measurement is made of a dye. Thus the instability and low extinction coefficient of NADH at 340 nm is eliminated as an assay limiting factor. Moreover many of the other mentioned problems are ameliorated or entirely eliminated.

DETAILED DESCRIPTION OF THE INVENTION

The present invention provides a method and analytical elements for assaying salicylate, catechol and other catechol generating substances. The method and elements are based on a series of enzymatic conversions. The chemical reactions involved are illustrated using salicylate. However it will be clear to all analytical chemists that this set of reactions can be easily adapted to the teachings herein for the analysis of catechol, any other catechol generating substance and the enzymes catalyst used in the reactions.

Salicylate hydroxylase in the presence of NADH converts salicylate to pyrocatechol (Eq. 1) which is oxidized by oxygen in the presence of tyrosinase to o-quinone (Eq. 2). The o-quinone is then quantitatively determined by the oxidation of a suitable leuco dye or the oxidative coupling of a developer and a coupler, to yield a dye (Eq. 3).

Equation 1):

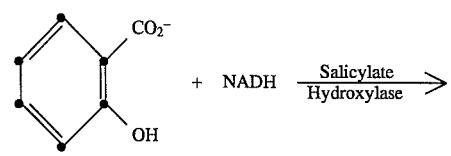

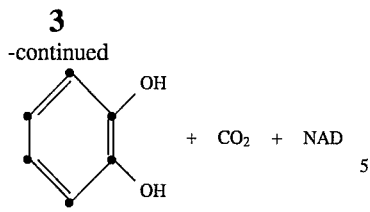

Equation 2):

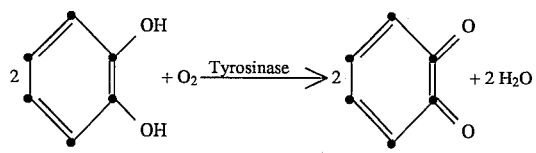

Equation 3):

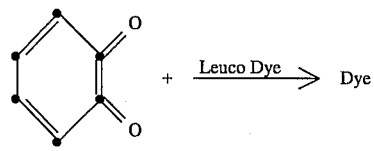

In versions of the elements for assay of catechol the assay is carried out by simple spotting of the sample on the element. In versions for assaying a catechol generating substances such as salicylate, the enzyme may be included in the element or added to the sample to be analyzed. In versions for assaying an enzyme the enzyme substrate may be added to the sample or to the element. The assays can be carried out both qualitatively and quantitatively in biological fluids in animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Examples of catechol generating substances other than salicylate are known. For example, o-hydroxyphenyl phosphate is hydrolyzed to catechol by alkaline or acid phosphatase. Tyrosine O-phosphate can be hydrolyzed by prostatic acid phosphatase. In each of the these hydrolyzations samples containing o-hydroxyphenyl phosphate and tyrosine can be assayed quantitatively. Indeed acid phosphatase can be assayed in a single step.

The various reagents used in the method and elements are available commercially. Tyrosinase is also available commercially.

Any leuco dye which changes from colorless to a measurable color will be useful in the present invention. Such dyes include triarylimidazoles and triarylmethanes compounds. A method for identifying useful dyes for detecting o-quinone and o-quinone generating materials such as catechol and salicylate is disclosed in U.S. Pat. No. 4,089,747. Useful leuco dyes are also disclosed in the latter patent. Thus leuco dyes from which useful substances for the present invention can be chosen, using an objective and easily performed test are well know in the analytical arts. Particularly useful dyes are triaryimidazoles, triarylmethanes and reduced indophenols.

Elements of the invention can be configured in a variety of forms, including elongated tapes of any desired width, sheets, slides or chips.

The elements can be used in manual or automated assay techniques. In general, in using the elements, assays are made by taking the element from a supply roll, chip packet or other source and physically contacting it with a sample (for example, up to 200 µl) of the liquid to be tested so that the sample and reagents interact sequentially within the element become mixed. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation, we simply mean that the reagents are maintained in contact with each other for a period of up to 5 minutes before color measurements are made.

The dry analytical elements of this invention are multi-layered. At least one of the layers has a spreading function as that function is known in the art. The layers include the reagents used in the method of the invention. The reagents are in two distinct layers or two distinct zones. The NADH is in a zone or layer separate from the other reagents except the leuco dye which can be in either zone or layer. All of the foregoing layers are coated on a support. The layers are generally in fluid contact with each other, meaning that fluids, reagents and reaction products (for example, color dyes) can pass or be transported between superposed regions of adjacent zones. In other words, when the element is contacted with an aqueous fluid, all reagents of the analytical composition of this invention mixed sequentially as stated hereinbefore and can readily move within the element as a composition. Each layer can be separate or two or more zones can be separate areas in a single layer of the element. Besides the references noted above, suitable element components are described also, for example, in U.S. Pat. Nos. 4,042,335 (issued Aug. 16, 1977 to Clément), 4,132,528 (issued Jan. 2, 1979 to Eikenberry et al), and 4,144,306 (issued Mar. 13, 1979 to Figueras).

Useful spreading layers can be prepared using fibrous materials, either mixed with a suitable binder material or woven into a fabric, as described in U.S. Pat. No. 4,292,272 (issued Sep. 29, 1981 to Kitajima et al), polymeric compositions or particulate materials, for example a blush polymer such as disclosed in U.S. Pat. No. 3,992,158, beads bound together with or without binding adhesives, as described in U.S. Pat. Nos. 4,258,001 (issued Mar. 24, 1981 to Pierce et al) and 4,430,436 (issued Feb. 7, 1984 to Koyama et al) and Japanese Patent Publication 57(1982)-101760. Particularly useful spreading layers comprise barium sulphate or titanium dioxide. Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The layers can be coated on transparent supports such as polyethylene terephthalate. Other supports are well known in the art.

The elements of this invention can also contain one or more other addenda commonly put in the elements for various manufacturing or operational advantages. Such addenda include surfactants, buffers, solvents, hardeners and other materials known in the art.

The following examples clearly establish the improved aspects of the present invention. Surfactants TX-100, TX-405, 10G, Alkanol XC and Zonyl FSN and the enzyme, tyrosinase and the other chemicals used in the following examples are all commercially available. Triton X-100 (TX- 100), and Triton X-405 (TX-405) are from Rohm and Haas; Peroxidase and Tyrosinase are from Sigma. The leuco dye used was 2-4(hydroxy-3,5-dimethoxyphenyl)-4,5-bis(4-dimethylaminophenyl)imidazole. Unless otherwise stated, all other materials were prepared by or obtained from Eastman Kodak Company

EXAMPLE 1

Determination of Salicylate Concentration on Element of Invention

The element used in this example had the following configuration and reagent content.

| | Concentration (g/m$^2$) | Preferred Concentration (g/m$^2$) |
|---|---|---|
| Reagent Layer: | | |
| Tyrosinase | 10,000–60,000 U/m$^2$ | 25,000 U/m$^2$ |
| K$_2$HPO$_4$ | 0.3–2.4 | 0.76 |
| KH$_2$PO$_4$ | 0.2–1.6 | 0.40 |
| 10G Surfactant | 0.03–0.25 | 0.11 |
| Reagent/Spreading Zone: | | |
| BaSO$_4$ | 50–175 | 108 |
| Cellulose Acetane | 0.4–1.2 | 0.6 |
| *Polyurethane | 1–5 | 1.08 |
| TX-100 | 0.2–2.5 | 1.35 |
| K$_2$HPO$_4$ | 0.4–3.5 | 1.15 |
| NaH$_2$PO$_4$ | 0.25–2 | 0.70 |
| **Dimedone | 0.08–1.44 | 0.32 |
| 932480* | 0.01–0.1 | 0.03 |
| 185421* | 0.6–1.8 | 1.08 |
| Sub Layer: | | |
| poly-n-isopropyl-acrylamide | 0.05–2.0 | 0.27 |
| Gelatin Layer (pH 7.0): | | |
| Gelatin | 3–20 | 10 |
| TX-100 | 0.01–0.1 | 0.03 |
| TX-405 | 0.01–0.1 | 0.03 |
| NaH$_2$PO$_4$ | 0.09–0.81 | 0.27 |
| ***MWaMt | 2–12 | 5 |
| SUPPORT | | |

*Polyurethane from B. F. Goodrich
**Antioxidant
***Copoly[methacrylamide-2-(sulfo-1,1-dimethyl-acrylamide,Na salt)-(2-acetoacetoxyethyl methacrylate)]

A separate series of solutions containing 1,2,4,6 and 10 mM/L of salicylic acid and NADH were combined in a volume ratio of 1:1. The result was a series of test solutions containing 0.5, 1.0, 2.0, 3.0 and 5.0 mM/mL of salicylic acid and NADH as shown in Table I. Each of the listed solutions in column A was combined with 1.0 mL of a solution containing 100 U/mL of salicylate hydroxylase. Each of the resulting solutions were spotted on separate dry analytical elements having the configuration and reagent content described above. The reflectance density at 670 nm for each solution is presented in Table I.

TABLE I

| Test Solution No. | Salicylic Acid Concentration mM/mL | Reflectance Density at 670 nm |
|---|---|---|
| 1 | 0.5 | .145 |
| 2 | 1.0 | .240 |
| 3 | 2.0 | .300 |

TABLE I-continued

| Test Solution No. | Salicylic Acid Concentration mM/mL | Reflectance Density at 670 nm |
|---|---|---|
| 4 | 3.0 | .405 |
| 5 | 5.0 | .535 |

The reflectance density shows that the method and element of this invention are well suited for assaying salicylate in aqueous fluids. Other experiments conducted with this same element show that it is all well suited for assaying catechol, including catechol generating substances.

EXAMPLE 2

Another element embodiment embodying the method of this invention is presented below.

| | Concentration (g/m$^2$) | Preferred Concentration (g/m$^2$) |
|---|---|---|
| TiO$_2$ Spreading Layer | | |
| Subbing Layer: | | |
| poly-n-isopropyl-acrylamide | I-100 Layer | Range (g/m$^2$) |
| Reagent Layer Zone 1: | | |
| Gelatin | 6.0 g/m$^2$ | 3–12 |
| Zonyl FSN (surfactant) | 0.03 g/m$^2$ | 0.01–0.2 |
| K$_2$HPO$_4$ | 1.40 g/m$^2$ | 0.7–2.3 |
| KH$_2$PO$_4$ | 0.13 g/m$^2$ | 0.06–0.19 |
| NaCl | 0.74 g/m$^2$ | 0.5–1.5 |
| bisvinylsulfonyl-methyl ether | 0.03 g/m$^2$ | 0.15–1.2 |
| NADH | 0.76 g/m$^2$ | 0.5–1.5 |
| Reagent Layer Zone 2: | | |
| Gelatin | 6.0 g/m$^2$ | 3–12 |
| Zonyl FSN (surfactant) | 0.03 g/m$^2$ | 0.01–0.2 |
| K$_2$HPO$_4$ | 1.40 g/m$^2$ | 0.7–2.3 |
| KH$_2$PO$_4$ | 0.13 g/m$^2$ | 0.06–0.19 |
| NaCl | 0.74 g/m$^2$ | 0.25–1.0 |
| Alkanol XC | 0.21 g/m$^2$ | 0.05–0.5 |
| Leuco-Dye | 0.53 g/m$^2$ | 0.2–0.8 |
| di-n-pentyl phenol | 5.35 g/m$^2$ | 2–8 |
| Dimedone | 0.13 g/m$^2$ | 0.05–0.3 |
| Salicylate Hydroxylase | 1,000 U/m$^2$ | 400–2,500 |
| TYROSINASE | 100,000 U/m$^2$ pH 7.6 | 25,000–150,000 |
| ESTAR | | |

A series of solutions were prepared containing 0.2, 1.4, 2.9, 4.3, 5.8 and 7.2 mM/L of salicylic acid (sodium salt). Each of the solutions was spotted on separate dry analytical elements having the configuration and reagent content described above. The reflectance density at 670 nm for each solution is presented in table II.

TABLE II

| Test Solution No. | Sodium Salicylate mM/ml | Reflectance Density at 670 nm |
|---|---|---|
| 1 | 0.2 | 0.22 |
| 2 | 1.4 | 0.36 |
| 3 | 2.9 | 0.38 |

TABLE II-continued

| Test Solution No. | Sodium Salicylate mM/ml | Reflectance Density at 670 nm |
|---|---|---|
| 4 | 4.3 | 0.43 |
| 5 | 5.8 | 0.45 |
| 6 | 7.2 | 0.47 |

The reflectance density again shows that the method and element of this invention are well suited for assaying salicylate in aqueous fluids.

The invention has been described in detail with particular reference to preferred embodiments thereof, but it will be understood that variations and modifications can be effected within the spirit and scope of the invention.

We claim:

1. A colorimetric method for quantitative assay of catechol or a catechol generating substance, comprising the steps of:

a) admixing a sample suspected of containing catechol or a catechol generating substance with NADH, tyrosinase, and a dye selected from the group consisting of diarylimidazoles, triarylimidazoles, triarylmethanes, and reduced indophenols; and b) determining the quantity of catechol present in the sample by colorimetric measurement.

2. The method of claim 1 wherein step a) further includes an enzyme for the conversion of the catechol generating substance to catechol.

3. The method of claim 1 wherein the catechol generating substance is selected from the group consisting of o-hydroxyphenyl phosphate and tyrosine o-phosphate.

4. A colorimetric method for a quantitative assay of salicylate comprising the steps of:

a) admixing a sample suspected of containing salicylate with, in any order or combination, NADH, salicylate hydroxylase, tyrosinase, and a dye selected from the group consisting of diarylimidizoles, triarylimidizoles, triarylmethanes, and reduced indophenols; and b) determining the quantity of salicylate present in the sample by colorimetric measurement.

5. The method of claim 4 wherein said dye is 2-(4-hydroxy-3,5-dimethoxyphenyl)-4,5-bis(4-dimethylaminophenyl)imidazole.

6. The method of claim 4 wherein the NADH is 1 to 2 mM/mL.

7. The method of claim 4 wherein the salicylate hydroxylase is 20 to 300 U/mL.

8. The method of claim 4 wherein the tyrosinase is 50 to 1000 U/mL.

9. The method of claim 4 wherein the dye is 0.2 to 10 µg/mL.

10. The method of claim 4 wherein said assay is conducted at a pH range of 6 to 8.5.

\* \* \* \* \*